United States Patent [19]

Hirshaut

[11] 4,283,497
[45] Aug. 11, 1981

[54] MICROBIOLOGICAL SYSTEMS

[75] Inventor: Yashar Hirshaut, Lawrence, N.Y.

[73] Assignees: Samson Helfgott; Jack W. Benjamin, both of New York, N.Y.; part interest to each

[21] Appl. No.: 6,005

[22] Filed: Jan. 24, 1979

[51] Int. Cl.³ ............................................. C12M 1/36
[52] U.S. Cl. .................................. 435/289; 435/291; 435/316
[58] Field of Search ............... 435/292, 293, 294, 297, 435/298, 299, 300, 301, 310, 313, 819, 315, 30; 137/806, 819, 823, 833, 834; 422/103, 100

[56] References Cited

U.S. PATENT DOCUMENTS

| | | | |
|---|---|---|---|
| 2,971,892 | 2/1961 | Carski | 435/298 |
| 3,158,553 | 11/1964 | Carski | 435/298 |
| 3,357,233 | 12/1967 | Roof | 137/819 X |
| 3,417,770 | 12/1968 | Denison | 137/806 |
| 3,484,207 | 12/1969 | Anthon | 422/103 X |
| 3,486,308 | 12/1969 | Burt | 435/292 X |
| 3,501,379 | 3/1970 | Tate | 435/291 |
| 3,533,428 | 10/1970 | Ruedle | 137/833 |
| 3,538,933 | 11/1970 | Miller | 137/806 |
| 3,567,389 | 3/1971 | Coulter et al. | 422/103 |
| 3,597,326 | 8/1971 | Liner | 435/298 |
| 3,778,351 | 12/1973 | Rosov | 435/30 X |
| 3,788,951 | 1/1974 | Pfordten | 435/30 |
| 3,830,701 | 8/1974 | Stussman et al. | 435/297 |
| 3,850,754 | 11/1974 | Wilkins et al. | 435/293 |
| 3,902,972 | 9/1975 | Beckford | 435/298 |
| 3,963,355 | 6/1976 | Aldridge et al. | 435/293 |
| 3,972,778 | 8/1976 | Cunningham | 435/293 |
| 4,012,288 | 3/1977 | Lyman et al. | 435/298 |
| 4,030,980 | 6/1977 | Beckford et al. | 435/298 |
| 4,072,577 | 2/1978 | Hirshaut | 435/297 |

Primary Examiner—R. B. Penland
Attorney, Agent, or Firm—Samson Helfgott; Jack W. Benjamin

[57] ABSTRACT

Microbiological systems for the automation of a microbiological laboratory including apparatus and methods for dilution of a microbiological sample, distribution of the sample to utilization devices, and application of the microbiological sample onto a growth medium in a sterile condition. In one embodiment, a fluid amplifier device is utilized for dilution of the microbiological sample and a fluid amplifier is also utilized for distribution of the diluted sample to a receiving well. In another embodiment, the microbiological sample is linearly applied to an elongated petri dish for subsequent incubation. Appropriate elongated petri dishes are described for use with such linear applications. A piston-cylinder arrangement is also provided for serial dilution of the samples.

13 Claims, 11 Drawing Figures

MICROBIOLOGICAL SYSTEMS

BACKGROUND OF THE INVENTION

This invention relates generally to microbiological systems, and more particularly to specific methods and apparatus for use in a microbiological laboratory for miniaturization and automation of microbiological procedures.

Microbiology laboratories are generally equipped with numerous apparatus for providing serial dilutions of the microbiological sample, distribution equipment for applying the diluted samples to appropriate growth medium, incubation equipment where the micro-organisms are permitted to grow on the medium, and various testing equipment to analyze the results of the growth. The various apparatus must generally be maintained in a sterile atmosphere to prevent cross contamination from other microbiological organisms. Although various automated equipment has been suggested for use in the microbiological laboratory, these equipment have been of extremely large scale and have been of limited value since many of them can perform only one small aspect of the microbiological laboratory. Much of the laboratory still relies upon individualized manual effort. As a result, the size of the microbiological laboratory is generally extensive, the number of personnel is quite high, and the cost of any analysis is excessive.

One of the reasons for the difficulty in miniaturizing and automating the microbiological laboratory involves the problem of providing appropriate dilutions of the microbiological sample. Generally, some form of serial dilution is required, typically a log distribution, in applying the sample onto a growth medium. This is generally achieved by the dilution of a sample and application of the diluted sample by means of a loop onto a growth medium utilizing a serpentine streaking onto a Petri dish. The automated equipment heretofore provided tried to mechanically duplicate the serpentine streaking onto the Petri dish. As a result, the size of the equipment needed was quite large and the speed was relatively slow.

A further problem with miniaturizing and automating the microbiological laboratory concerned the distribution of diluted samples into receiving wells. Although small receiving wells could be achieved on a single array, the problem faced was how to apply the exact amount of diluted sample to each receiving well. Various prior art apparatus utilized an injection principal which filled the receiving wells in a stepwise manner. This process was slow and again required large size equipment.

Numerous other problems unique to the microbiological laboratory have prevented the automation and miniaturization of the equipment needed. For example, the need for maintaining the equipment in a sterile atmosphere provided specific restraint which prevented direct application of automatic equipment from other laboratories into the microbiological field. Additionally, the necessity for providing the serial dilution of the sample provides an increased time and space problem not necessarily required in other scientific laboratory work. Accordingly, while other fields of medicine, such as biochemistry, have advanced to the state of automation and miniaturization, the microbiological laboratory has yet to achieve the advanced state of progress which has been available in related fields of medicine.

SUMMARY OF THE INVENTION

According to the present invention, there is provided a microbiological device for use in dilution or distribution of a microbiological sample. At least one fluid amplifier is utilized wherein the fluid amplifier includes a control chamber, an inlet port for feeding a working fluid into the control chamber, two fluid outlet ports for selectively discharging the contents of the control chamber, and a control port means fluidly coupled to the control chamber for utilizing a control fluid to direct at least a portion of the working fluid to the selected outlet port. A supply means provides the working fluid in the form of a microbiological sample to the inlet port. A utilization means receives the working fluid from the selected outlet port and can utilize it for microbiological use.

When utilized as a dilution device, the supply means includes two inputs fluidly coupled to the fluid amplifier inlet ports whereby the supply means provides the microbiological sample to one of the inputs and provides a fluid diluent to the other of the inputs. The control chamber serves as a mixing chamber to dilute the sample. In addition to the single fluid amplifier, a plurality of such amplifiers can be connected in series to provide the desired serial dilution.

When utilized as a distribution device, there is further included a selector which is coupled to the control port means for initially directing all of the sample to one outlet and subsequently switching the sample to the other outlet to discharge a constant quantity of the sample to a receiving well. A plurality of the fluid amplifiers can be connected in series to provide substantially equal distributions to the receiving wells.

The dilution and/or distribution devices can be included directly into the cover portion of a large Petri dish wherein the lower portion has an array of receiving wells to receive the serially diluted samples therein.

A further embodiment of the microbiological system of the present invention includes a method and apparatus for linear streaking. The apparatus operates in a sterile condition and conveys an elongated tray having growth medium thereon to an application stage. At the application stage a microbiological sample is linearly applied onto the growth medium in the elongated tray. The elongated tray is removed from the application stage and a cover is placed onto the elongated tray.

A linear Petri dish is also provided for use in the linear streaking system and includes a rectangular base plate for receiving a growth medium thereon. Side walls are formed around the base plate and a cover member is removably positioned over the side walls for permitting an indirect flow of air to the growth medium. In an embodiment of the invention, the side walls are retained as part of the cover member and are placed over the rectangular base plate.

The method of linear streaking is also covered whereby a plurality of elongated microbiological trays having growth medium thereon are utilized. The trays are arranged in a predetermined sequence and the microbiological sample is linearly applied to the growth medium in the trays whereby the contents of each successive tray has a different relationship between the sample and the growth medium as compared to the preceeding tray.

In order to achieve serial dilution, the microbiological system can also include a piston and cylinder device with the piston movable in the cylinder by means of a rod coupled to the piston and extending through cylinder. An outlet port is provided at one end of the cylinder. A first inlet is provided intermediate the outlet and the piston for receiving a microbiological sample. A second inlet on the opposite side of the piston receives diluent. A one-way passage is provided from one side of the piston to the other. In this manner, reciprocation of the piston provides a serially diluted sample at the output of the cylinder.

It is therefore an object of the present invention to provide improved microbiological devices, as described above, which can be utilized as part of a microbiological system in automating a microbiological laboratory and which avoids the aforementioned problems of the prior art.

A further object of the present invention is to provide a microbiological device utilizing a fluid amplifier for controlling the flow of the microbiological sample.

Yet another object of the present invention is to provide a microbiological dilution device utilizing a fluid amplifier for controlling the dilution of the microbiological sample.

A further object of the present invention is to provide a microbiological device providing serial dilution of a microbiological sample and utilizing a plurality of serially connected fluid amplifiers.

Yet a further object of the present invention is to provide a microbiological distribution device utilizing a fluid amplifier for providing distribution of a microbiological sample.

Still another object of the present invention is to provide a microbiological distribution device having a plurality of serially connected fluid amplifiers for providing substantially equal distributions of a microbiological sample to receiving wells.

A further object of the present invention is to provide a microbiological device such as a large Petri dish having an array of receiving wells in the base portion and having a dilution and/or distribution mechanism in the cover portion.

Yet another object of the present invention is to provide for the use of a fluid amplifier in a microbiological device wherein the fluid sent through the fluid amplifier is utilized as the working fluid.

A further object of the present invention is to provide a method of linear streaking of Petri dishes.

Yet a further object of the present invention is to provide for the simulation of the standard serpentine streaking by utilizing linear segments for the application of a microbiological sample.

A further object of the present invention is to provide an apparatus for linear streaking of microbiological samples onto a growth medium.

Another object of the present invention is to provide a linear Petri dish for use in the linear streaking of microbiological samples.

Still a further object of the present invention is to provide a method of linear streaking.

Another object of the present invention is to provide a piston and cylinder arrangement for use as a serial dilution device.

These and other objects, features and advantages of the invention will, in part, be pointed out with particularity, and will, in part, become obvious from the following more detailed description of the present invention taken in conjunction with the accompanying drawings, which form an integral part thereof.

BRIEF DESCRIPTION OF THE DRAWINGS

In the various figures of the drawing, like reference characters designate like parts.

In the drawings.

DESCRIPTION OF THE PREFERRED EMBODIMENTS

In order to provide automation and miniaturization to the microbiological laboratory, it is necessary to provide for various microbiological systems that can be easily manufactured, occupy little space, are reliable, and can provide exact, reproducible results. In most cases, apparatus introduced into the microbiological laboratory were variations of corresponding equipment utilized in other medical laboratories. However, it has been found that a particular device can have unique applicability to the microbiological laboratory even though heretofore its use has been associated with a complete different technology and its applications thus far have been completely foreign to medical use.

In the field of electronics there has recently developed a technology utilizing fluid logic elements. Such elements are broadly designated as "fluid amplifiers" and can be combined to provide various logic elements to simulate electronic circuits. The logic functions are carried out by an interaction between jets of air or liquid and the device contains no moving parts or electronic circuits.

Typically, a fluid amplifier includes a control chamber with an inlet port for feeding a fluid into the control chamber. Two fluid outlet ports are provided for discharging the contents of the control chamber. Control ports are fluidly coupled to the control chamber and can direct a control fluid to the control chamber. By way of example, the fluid passing into the inlet port can be water which is controlled by a stream of air utilized in the control ports. By controlling the air pressure at either of the control ports, the water can be selectively directed to either of the outlet ports.

In the analog type fluid amplifier, the amount of water discharged at each of the fluid outlet ports can be selectively controlled as desired. In a digital type fluid amplifier, the liquid is discharged from only one of the outlet ports which is controlled by the air stream to effectively provide a switch between the two outlet ports.

The fluid amplifiers have been combined in series, stacked, placed in parallel, and interconnected to produce numerous mathematical logic functions. It has even been suggested to provide a fluid computer utilizing such fluid amplifiers. The fluid amplifier can be formed in an extremely thin plastic layer and occupies extremely little space and many such fluid amplifiers can be stacked together occupying minimum size and requiring inexpensive manufacturing costs.

Further information on fluid amplifiers can be obtained in numerous textbooks, patents, and technical and trade journals. By way of example reference is had to the textbook "Fluid Amplifiers," by Joseph M. Kirshner, McGraw-Hill Company, 1966.

The prior art utilization of fluid amplifiers used the liquid passing through the fluid amplifier only as an indicator of the analog or digital result. In the case of the digital fluid amplifier, the only interest was into which outlet port the liquid passed. The specific liquid utilized was of relative unimportance. The liquid itself was only used as a means for providing the indication. The fluid amplifier itself was not utilized to provide any direct action onto the fluid and heretofore the fluid itself was not used for any positive purpose in itself.

It has been found, that the fluid amplifier can actually be utilized as a basic tool in a microbiological system whereby the fluid amplifier can serve as the basic element for either dilution of a microbiological sample and/or distribution of the sample to appropriate receiving wells. Thus, the essential concept is to utilize the fluid amplifier to act upon the fluid whereby the fluid itself becomes a working fluid which is acted upon and subsequently utilized for further testing. Thus, the present invention teaches to provide as the fluid in the fluid amplifier a microbiological sample which passes through the fluid amplifier and is either diluted within the fluid amplifier by a diluent and/or can be distributed by the fluid amplifier to appropriate receiving wells.

Figure 1:
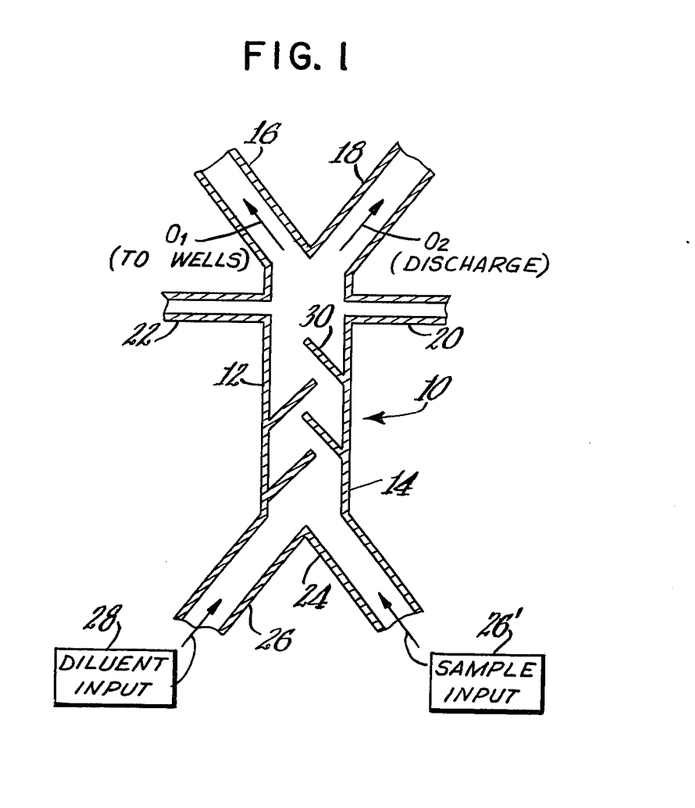
FIG. 1 is a schematic drawing of a fluid amplifier utilized as a single stage of dilution of a microbiological sample.

Referring now to FIG. 1, there is shown an embodiment utilizing the fluid amplifier to provide a single stage of dilution of a microbiological sample. The fluid amplifier shown generally at 10, includes a control chamber 12 through which the fluid enters through an inlet port 14. Two fluid outlet ports 16, 18, are connected to the control chamber for selectively discharging the contents of the control chamber. Control ports 20, 22 are fluidly coupled to the control chamber. A control fluid, such as air, is directed selectively through the control ports to direct at least a portion of the working fluid from the control chamber into the fluid outlet ports 16, 18.

Two inputs 24, 26 feed into the inlet port 14. A supply means 26' provides a sample input through the input 24 while a further supply means 28 provides a diluent to the input 26. The sample and the diluent are sent through their respective inputs and reach the control chamber which serves as a mixing chamber to dilute the sample with the diluent. The diluted sample is then appropriately controlled by means of the control ports 20, 22 to selectively discharge a desired amount of the diluted sample through the outlet port 16 as the output O1 which can be sent to receiving wells. The remainder of the diluted sample designated as output O2 can be sent through the outlet port 18 and can be discharged. In order to improve the mixing, baffles 30 are placed within the control chamber.

It is understood that the drawing shown in FIG. 1 is only schematic and that the fluid amplifier itself would be formed within a plastic or glass medium in accordance with well known fluid amplifier technology. Furthermore, the appropriate ports, are all in accordance with the well known fluid amplifier technology and the air pressures would be controlled in accordance with such known teachings. The supply means for supplying the sample and diluent can be any of the well known supply devices presently utilized in microbiological technology including injection means, pumps, nozzles, etc. The percent dilution can be controlled by controlling the relative concentrations of the sample and the amount of diluent to provide any dilution percentage desired. The portion of the output can be selectively chosen as a desired percent of the total amount of diluted sample. The output selected can be directed to receiving wells directly or through a distribution system. The portion discharged can be sent through additional series of dilutions by means of further fluid amplifiers each further diluting the sample in accordance with desired concentration ratios.

Figure 2:
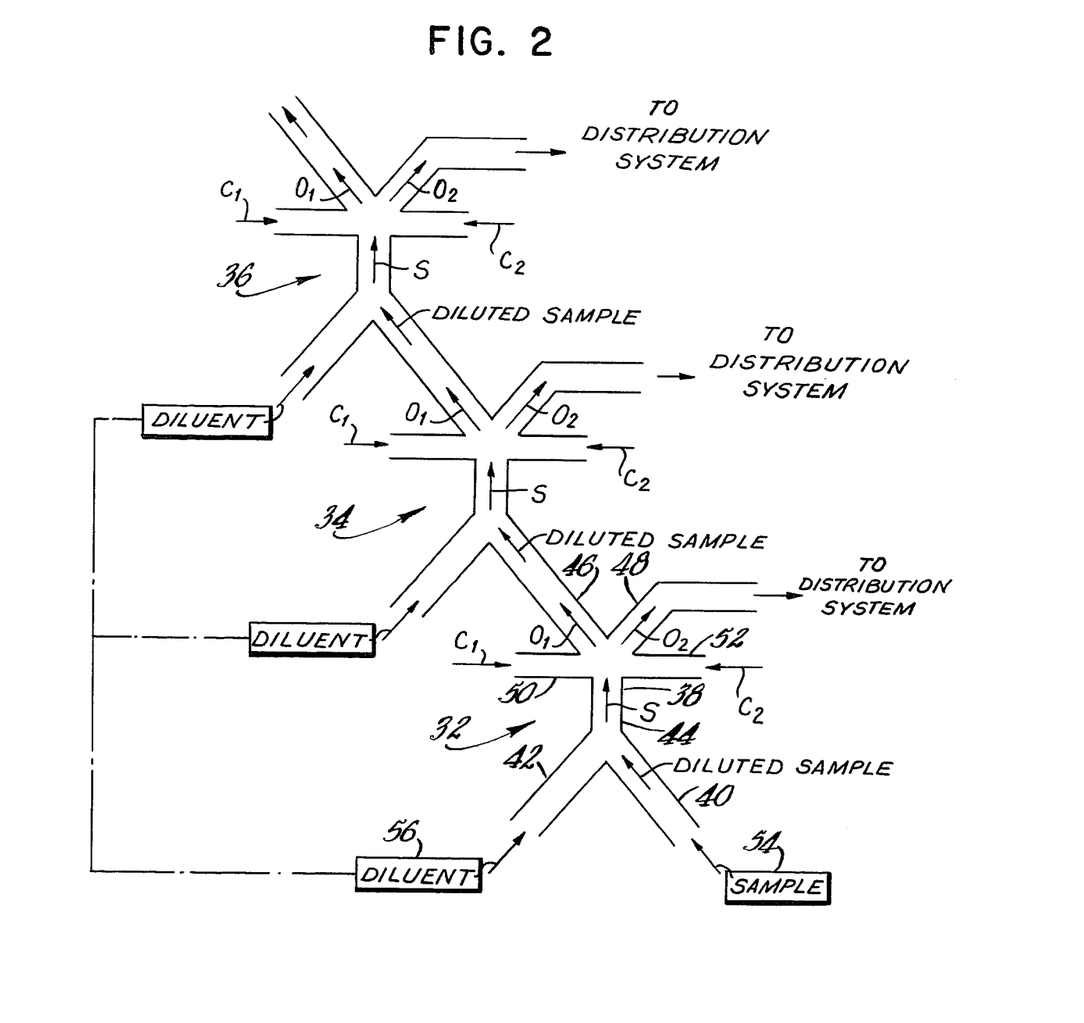
FIG. 2 is a schematic drawing showing a series of interconnected fluid amplifiers for use in serial dilution of a microbiological sample.
Figure 3:
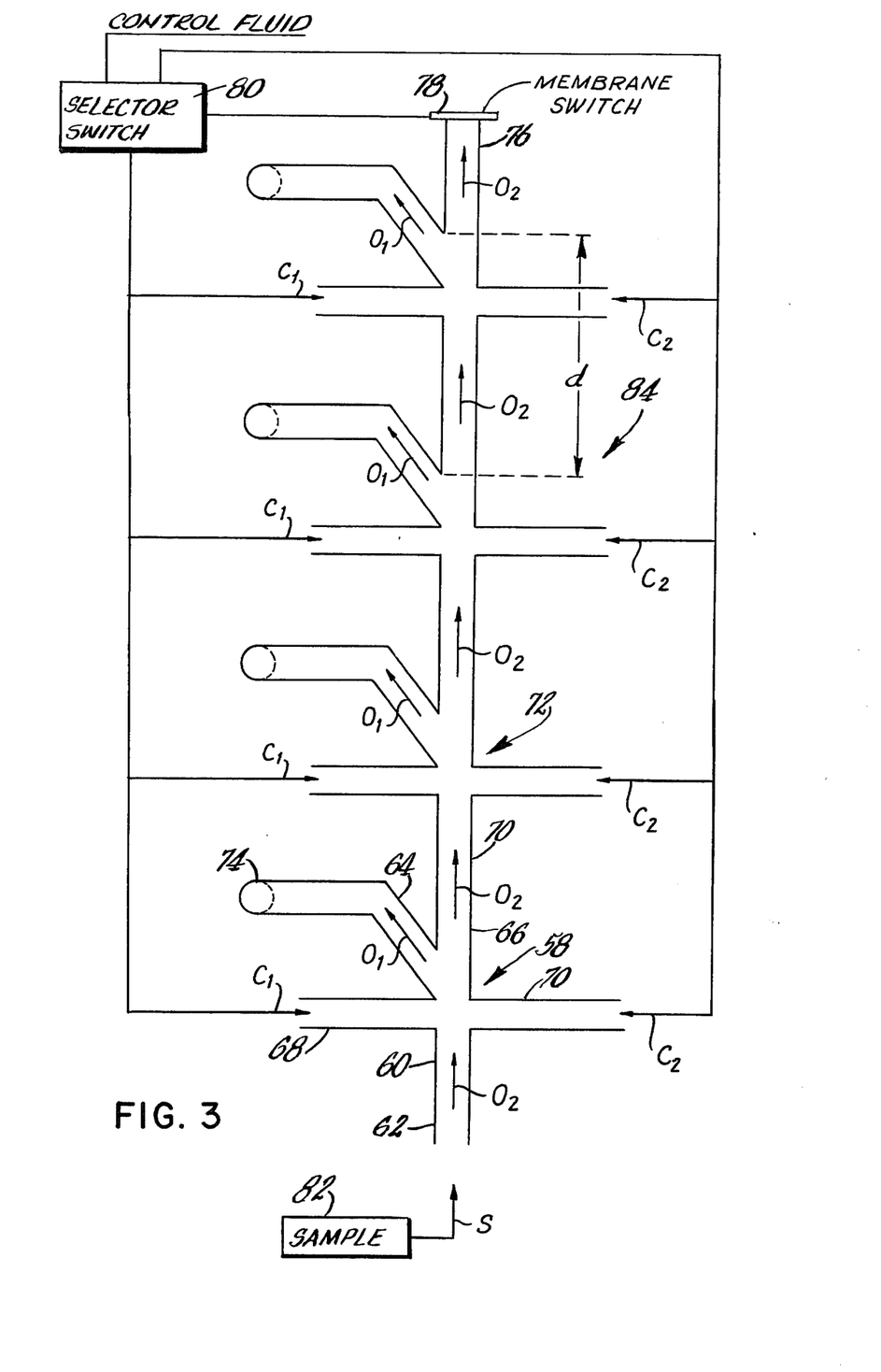
FIG. 3 is a schematic drawing of a series of interconnected fluid amplifiers utilized for the distribution of microbiological samples.

Referring now to FIG. 2, there is shown a series of interconnected fluid amplifiers of the type described in FIG. 1 wherein the amplifiers are connected to provide serial dilution of the initial sample. As is shown schematically in FIG. 2, there are three stages of fluid amplifiers 32, 34, 36. Each fluid amplifier includes a control chamber 38 with two inputs 40, 42 respectively feeding into an inlet port 44 at the entrance of the control chamber. Outlet ports 46, 48 can selectively discharge the fluid from the control chamber. Control ports 50, 52 feed a control fluid into the control chamber to selectively direct at least a portion of the fluid into the desired outlets.

One outlet 48 from each fluid amplifier feeds a distribution system. The other outlet 46 feeds into one of the inputs of the next stage fluid amplifier.

A sample is provided from a supply means 54 at one input 40 of the first stage. The one input of each successive stage is fed with the output from the previous stage. Diluent is fed to the other input of each of the stages. The diluent comes from a supply means 56 and can be the same supply means for all of the stages. Thus, a common diluent supply can be utilized and fed into each of the other inputs of all stages.

The sample provided to the first stage is diluted by a desired percent by controlling the concentration of the sample and the amount of diluent. The amount desired for usage is controlled by the control ports and that portion is sent to the distribution system for utilization. The remaining diluted sample passes to the next stage where additional diluent is provided to lower the concentration of the sample by further diluting it. A portion of that further diluted sample is then selected for distribution with the remainder passing onto the next stage for still further dilution. This can continue for numerous stages in accordance with the number of dilutions and steps desired.

It is accordingly appreciated that by serially interconnecting the fluid amplifiers a serial dilution of the original sample can be achieved at each successive stage of the fluid amplifier system. The amount selected for the distribution system can be identical at each stage whereby the same amount of diluted sample of each serial dilution step can be tested. The control fluid, such as air, can be appropriately selected to produce the desired amount for the distribution system and can be simultaneously controlled for all of the stages. Baffles or similar mixing means could be included in the control chambers of each stage to further insure proper mixing of the sample with the diluent to achieve proper dilution at each stage.

The fluid amplifier can be utilized not only for single stage of serial dilution but could also be used as part of a distribution system for distributing the sample itself or the diluted sample to appropriate receiving wells, test tubes, or other receiving means. Referring now to FIG. 3, there is shown the use of the fluid amplifier in a microbiological distribution system. A series a four fluid amplifiers are shown serially interconnected. The first fluid amplifier shown generally at 58 includes a control chamber 60 having an inlet port 62 with two outlet ports 64, 66. Control ports 68, 70 feed the control fluid to the control chamber to selectively direct the fluid to the various outlet ports. One outlet port 66 of the first stage feeds the inlet port 70 of the next fluid amplifier 72. In a similar fashion, one outlet port of each stage feeds the inlet port of the next successive stage.

At the end of the other outlet port 64 is a discharge port 74 where the microbiological fluid can be discharged to a receiving well or other receiving means. At the end of the outlet port 76 of the last fluid amplifier stage is a detector shown as the membrane switch 78 which can detect when fluid has passed through the last stage. The control fluid, such as air, is provided as the control fluid C1, C2 and is selected by means of the selector switch 80. The switch can be a control valve which receives the control fluid, such as air, and selectively sends the fluid into the C1 ports of all the amplifiers whereby the fluid is directed to the output 02 of the amplifiers, or can switch the control fluid to the control ports C2 whereby the fluid will pass to the outputs 01 of each amplifier.

In operation, a supply means 82 provides the microbiological sample in original or diluted form to the first stage of the amplifiers. The control fluid is directed through inputs C1 whereby the sample will pass to the output 02 of the first stage and from there feed into the next stage. Continuous feeding of the sample into the distribution system will cause the fluid to continuously flow through the outputs 02 of the successive stages until it completely fills the stages and reaches the detector 78. The detector responding to the complete filling of all stages will signal the selector switch to switch the control fluid to the control C2 of each stage whereby the fluid will be switched at each stage from the outlet 02 to the outlet 01. Each outlet 01 is associated with a receiving well whereby the contents of each section of fluid amplifier will flow into the receiving well.

It should be appreciated, that by making the size of each of the fluid amplifiers substantially identical, a substantially identical amount of the sample will be distributed to each of the receiving wells. Specifically, referring to the stage 84, the fluid filling the distance d from the inlet port of the control chamber to the outlet ports will be identical as the corresponding distance for all of the stages. The microbiological fluid filling that portion will be discharged into the receiving wells. However, the amount of microbiological fluid in each stage filling the corresponding portion will be substantially identical. Accordingly, a substantially equal amount of microbiological fluid will be discharged by means of the distribution system shown in FIG. 3.

The size of the fluid amplifier utilized for dilution and/or distribution is small enough whereby the series of fluid amplifiers connected for dilution and/or distribution can be directly built into the cover portion of a Petri dish having an array of receiving wells. In this manner, the microbiological sample can be sent directly into the cover portion of a Petri dish for dilution and subsequent distribution to receiving wells directly beneath the cover.

By way of example, FIG. 4 schematically shows a distribution system using fluid amplifiers which is built into the cover portion of a Petri dish whereby the diluted sample can be fed into the cover and distributed in equal amounts to receiving wells in the lower portion of the Petri dish. The Petri dish is shown generally at 86 and includes the cover portion 88 and the lower portion 90. An array of receiving wells 92 are formed in the lower portion. Each receiving well can typically include a growth medium. Alternately, the lower portion can be a holder for a series of test tubes whereby the distribution will be directly into the test tubes. Similarly, distribution can be into any other array of receiving means built into or connected to the lower base portion 90.

The upper portion 88 is shown to include three parallel paths 94, 96, 98 of fluid amplifiers with four fluid amplifiers in each parallel path. Specifically referring to the path 94, the first fluid amplifier on the left of that path has a control chamber 100 with an inlet port 102 and a first outlet port 104 feeding into the next inlet 106 of the next control chamber 108. The second outlet of the first amplifier 110 includes a discharge port 112 which is disposed over a corresponding receiving well so that the fluid can be directed to the receiving well therebeneath. The control ports 114, 116 are fluidly connected to the control chamber 100 for directing the microbiological sample to the respective outlet ports.

The diluted sample is fed through an inlet coupler 120 into the distribution system. Air for one control port is sent through the air coupler 122 and air for the other control port is sent through the coupler 124. The diluted sample which is not distributed is discharged through the coupler 126. Initially, the diluted sample is sent in through 120 with the air pressure through 124 being greater than the air pressure through 122. In this way the diluted sample will pass serially from one stage to the next stage and fill all three parallel paths until the fluid continues through the discharge coupler 126. The portion filled by the fluid is shown with dots for clarity. When the diluted sample completely fills the main paths of the fluid amplifiers, the pressure of the air is switched whereby the pressure is greater through the coupler 122 whereby the diluted sample from each stage of the amplifier will be sent to the opposite outlet ports and be discharged into the receiving well therebeneath. As heretofore explained, a substantially identical amount of fluid will be passed out of each stage whereby a substantially identical amount of the diluted sample will be received by each of the wells.

In addition to the distribution system shown built into the cover, the dilution system heretofore described could also be built into the cover as an upper layer or as an adjacent section. In this way, an initial sample can be fed into the cover portion of the Petri dish together with diluent and directly within the cover portion the sample will be serially diluted and appropriately distributed to receiving wells in the lower portion of the Petri dish. The size of the Petri dish can be maintained small and the entire dilution and distribution process is automated and achived in a succeedingly fast time.

Figure 4:
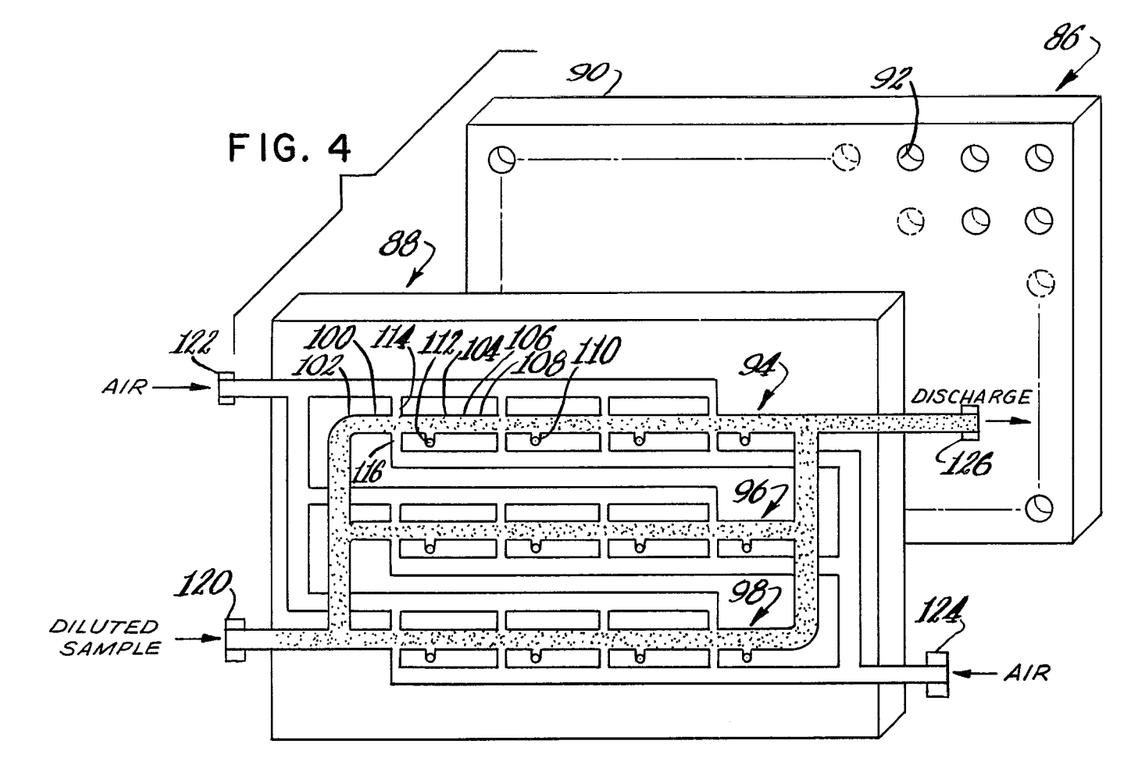
FIG. 4 is a schematic drawing showing a plurality of serially interconnected paths of fluid amplifiers as incorporated in the cover of a Petri dish for use in the distribution of microbiological samples to receiving wells.

The entire Petri dish can be connected to a holder with appropriately maintained sterile valve connections for feeding the sample, diluent, and air, etc., into the Petri dish. The feeding of successive Petri dishes can be automatic into the holding mechanism and as each Petri dish is fed into the holder the appropriate sample and diluent are fed into the cover portion and the air appropriately controlled for the proper dilution and distribution. After complete distribution of the diluted sample to the receiving wells, the Petri dish is automatically removed and a subsequent dish placed into the holder. The necessary sterility can be maintained throughout. Where different samples are introduced for each Petri dish, appropriate sterilization of the necessary valves can be carried out between successive operations.

A further aspect of the microbiological system for automation and miniaturization for a microbiological laboratory concerns the concept of linear streaking. Heretofore in prior art microbiological use, it has been common practice to provide a serpentine streaking of a sample on a Petri dish in order to achieve proper progressive dilutions of the sample on the growth medium. Typically, a microbiological sample will be diluted and by means of a loop a quantity of sample will be held and the loop will be streaked across a circular Petri dish. The streaking brings about the progressive dilutions of the sample on the growth medium.

Even when automating the microbiological laboratory, heretofore automatic equipment has been provided which will automatically provide the serpentine streaking of the dish. These automated equipment have been expensive and difficult to control and accordingly, have not been widely utilized.

The present invention provides the concept of linear streaking in place of the heretofore accepted serpentine streaking. Thus, an elongated Petri dish can be provided and an appropriate sample linearly applied onto the elongated Petri dish. The Petri dishes can be placed in a sequence whereby a series of applications of the sample are applied in sequence onto the dishes.

Figure 5:
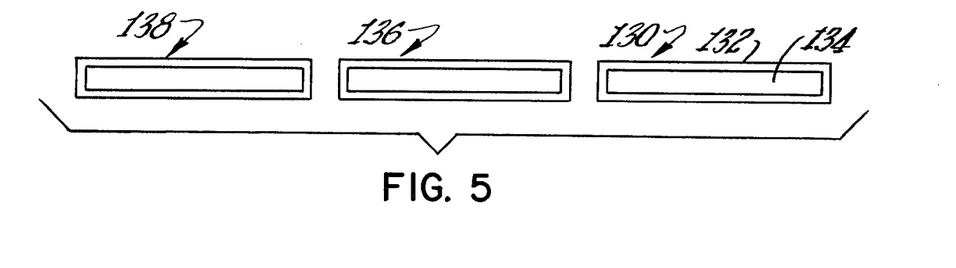
FIG. 5 shows a sequence of linear Petri dishes, in accordance with the present invention.

Referring now to FIG. 5, there is shown three elongated Petri dishes in sequence, the first of which is designated as 130. Viewing the dishes from above, there is a base plate 132 on which is provided a growth medium 134. The subsequent dishes 136 and 138 can be interconnected or spaced apart from each other. The microbiological sample would be applied linearly across each of the three elongated Petri dishes.

In one variation, a microbiological sample either directly or diluted, will be applied respectively to all of the Petri dishes. However, each elongated Petri dish will have a different type of growth medium. With the same sample applied to various growth mediums, it will be possible to determine the type, content, etc. of the sample viewing its reaction to the various growth mediums.

In another variation, each of the elongated Petri dishes would have the same type of growth medium. An applicator would be utilized which continuously diluted the microbiological sample whereby a different concentration of the microbiological sample is provided successively to the various elongated trays.

Figure 6:
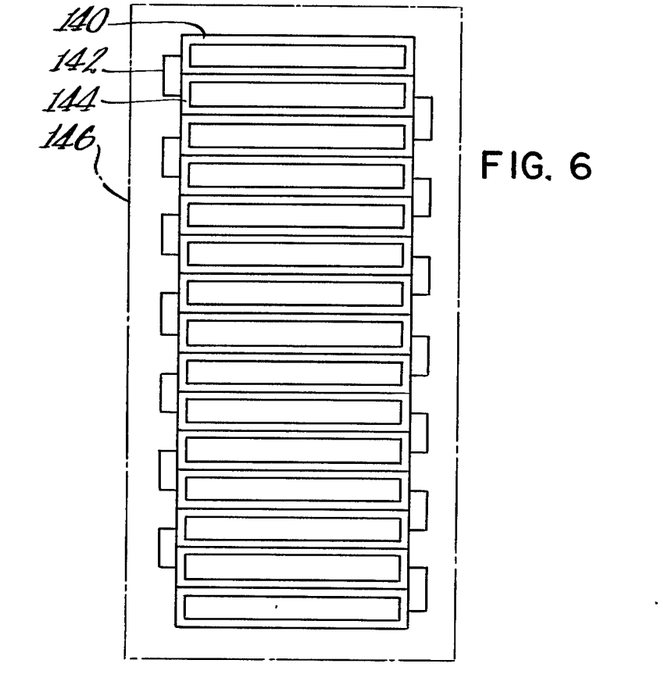
FIG. 6 schematically shows a top view of a sequence of interconnected linear Petri dishes coupled in a serpentine fashion.

After the elongated trays or Petri dishes have received the appropriate microbiological sample, the trays can be arranged in a desired pattern. For example, as shown in FIG. 6, each tray 140 has a coupling connector 142 at one end thereof. The coupling connector can interconnect to the next adjacent tray 144. All of the trays are thereby interconnected in serpentine fashion and can be contained within a single area 146. Thus, effectively, by utilizing linear streaking with short strokes on elongated trays, the serpentine arrangement can be simulated not by providing a serpentine streak on a Petri dish, but providing linear segments and then arranging the trays in a serpentine fashion.

Of course, the elongated trays need not be arranged in serpentine fashion but can be placed serially, in parallel or arranged in any other pattern. Furthermore, the trays need not necessarily be elongated but can be square, or other shape, as long as they can receive a linear application of the microbiological sample.

Figure 7:
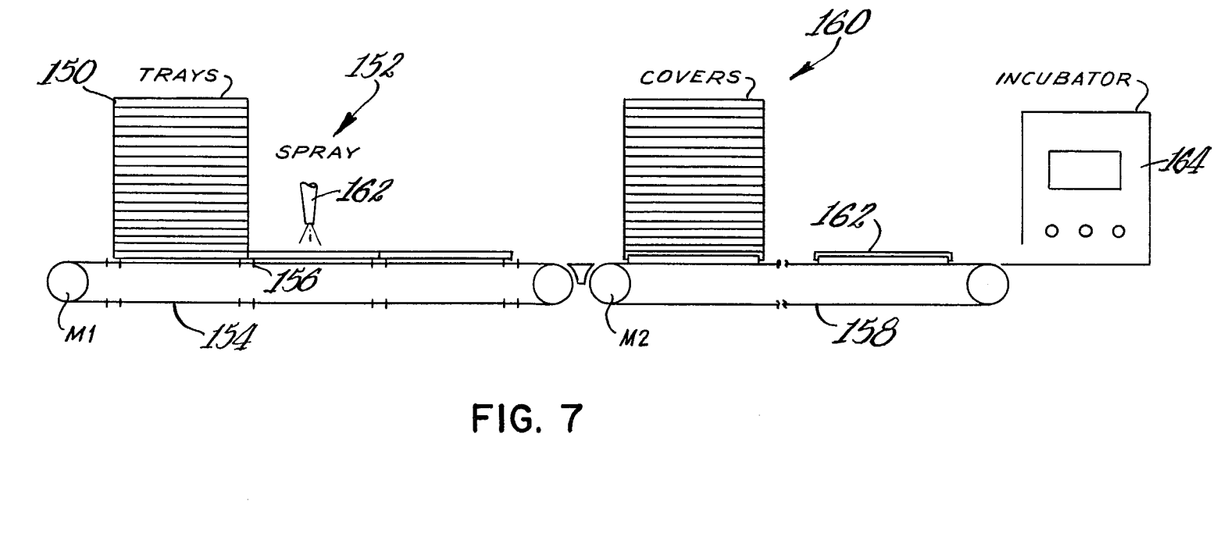
FIG. 7 schematically shows apparatus for linear streaking in accordance with the present invention.

Referring now to FIG. 7, there is shown a simple, schematic of an apparatus for linearly applying the microbiological sample onto trays. Initially the trays are stacked at 150. The trays can be either individually placed in a sterile condition or can be provided with a plurality of sterile trays contained in a single package. However, from their stacked arrangement, each of the trays are individually fed to an application stage 152 in which the microbiological sample is linearly applied to the trays.

The movement is shown by means of a conveyor belt 154 having grasping pins 156 which matingly grasp each tray and move it through successive stages. A first motor M1 moves a first section of the conveyor belt and a second motor M2 moves a second section 158 of the conveyor belt which removes the trays from the application stage and sends it to a covering stage 160 where covers are applied.

In the application stage 152 there is shown a spray head 162 for linearly spraying the trays. The spray head can be maintained stationary with the trays providing linear movement therebeneath. Alternately, the trays can be held in place or moved slowly and the spray head can also linearly spray the medium onto the trays.

The spray head 162 can be the output of a serial dilution system whereby each successive tray receives a different concentration of the microbiological sample. One such serial dilution system which can feed the spray head is of the type heretofore described utilizing fluid amplifiers. Another serial dilution system is of the type which will be described in connection with FIG. 11. A further type of serial dilution system can include a central chamber with radially extending outlet arms in the form of a central hub with outwardly extending spokes. The sample is initially fed into the central chamber and at each spoke a successive amount of diluent is fed. The distal ends of each outlet arm approaches the spray head and provides successive increased dilution of the sample. Other types of serial dilution devices can also be utilized. However, with those heretofore described there can be an exact control of the dilution in order to achieve a desired amount.

Specifically, with heretofore designed serpentine streaking arrangements, the exact concentration at any particular point in the serpentine streak was not directly known nor could it be reproduced. With the present linear streaking, at each linear section there can be provided a controlled dilution which can be measurably reproduced and can be predetermined and calculated. For example, any desired geometric progression of serial dilutions can be achieved. A logarithmic dilution can be provided over a very short area with the exact concentration of the sample at each section being specifically known and calculatable. Of course, continuous dilutions could also be used.

Referring again to FIG. 7, each of the trays move along the conveyor belt and receive a linear application of the medium from the spray head or other applicator. The trays move onto the next conveyor section 158 where they move under the covering section 160 where covers 162 are placed on each tray. The trays can then be placed in any of the patterns, as was described in connection with FIG. 6 and can then be fed into an incubator 164.

Figure 8:
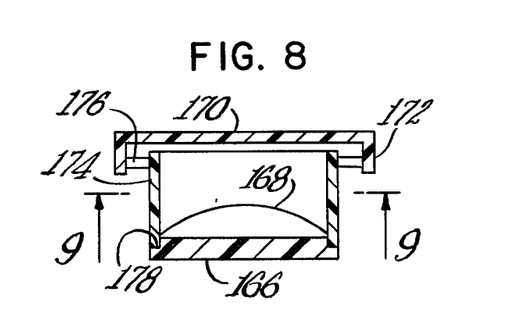
FIG. 8 shows a sectional elevational view of the embodiment of a linear Petri dish in accordance with the present invention.
Figure 9:
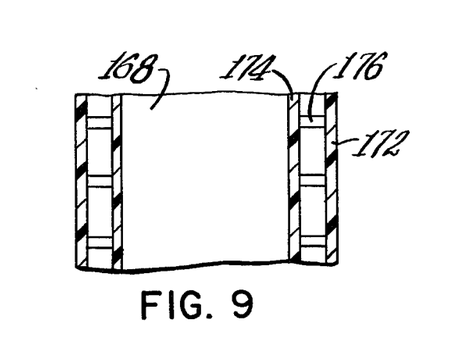
FIG. 9 shows a fragmentary sectional view taken along line 9—9 of FIG. 8.

One arrangement of the trays which can be utilized in conjunction with the system described is shown in FIGS. 8 and 9. The tray itself includes a base 166 on which is placed the growth medium 168. The covers include an upper flat plate 170 with downwardly depending flanges 172 along the periphery. The side walls 174 of the base are supported by the cover means by means of inwardly extending struts 176. The walls 174 fit into receiving seats 178 formed on the base 166.

Thus, the tray itself only includes the base plate with the growth medium formed directly thereon. These base plates pass beneath the applicator for linear application of the microbiological sample. Then, they receive the covers with the downwardly depending sidewalls whereby the side walls fit into receiving seats on the base plate and a petri dish is formed. It should be appreciated that the struts are spaced apart from each other and permit an indirect flow of air therebetween to reach the growth medium to provide the necessary flow of air needed for the incubation.

At the same time, because of the top plate there is sufficient sturdiness to permit stacking of the elongated Petri dishes after they have been innoculated by means of the microbiological sample.

It should further be appreciated that although initially only a linear tray is provided with a growth medium thereon, after application of the cover which fits onto the base plate there is formed a complete conventional Petri dish having the necessary indirect flow of air.

Figure 10:
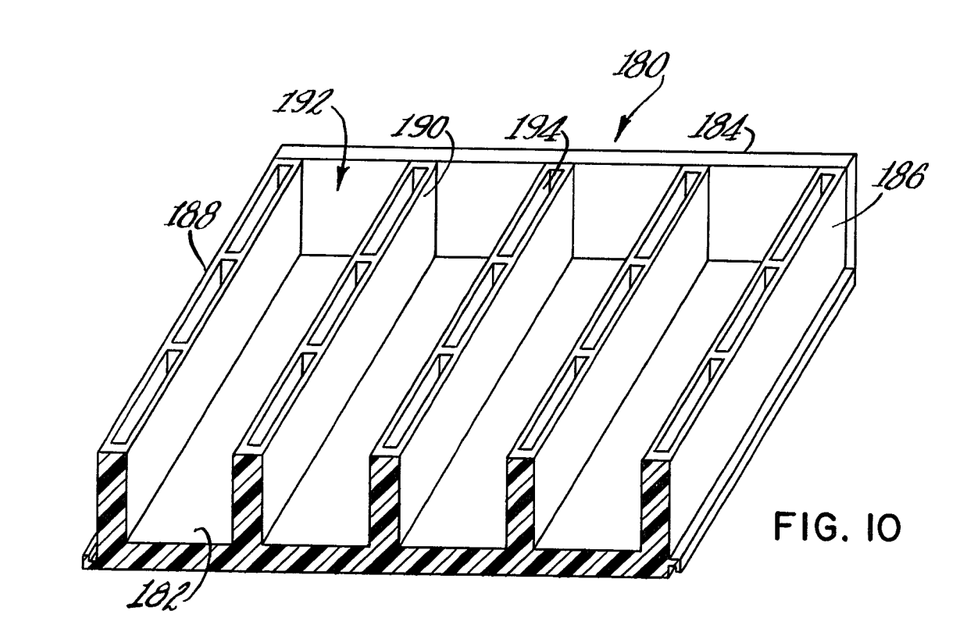
FIG. 10 is a schematic isometric drawing showing another embodiment of the linear Petri dish in accordance with the present invention.

In addition to using a Petri dish with one section, it is possible to have a plurality of sections in parallel relationship on a single such Petri dish. Referring now to FIG. 10, there is shown a portion of such Petri dish generally designated as 180 and including a base plate 182 with at least a rear wall 184 and longitudinally extending walls 186 and 188 at the respective ends as well as intermediate walls 190 to separate the dish into a plurality of sections 192. A growth medium would be placed in each of the sections 192. The intermediate walls include passageways 194 which can receive a laminar flow of fluid therethrough to maintain each of the longitudinal sections sterile from the next adjacent section.

Utilizing the Petri dish of the type shown in FIG. 10, it is possible to simultaneously apply a microbiological sample along a plurality of channels within the same dish. The sample would be linearly applied across the individual longitudinal sections and by means of the laminar flow of fluid cross contamination between the adjacent sections would be prevented. Each adjacent section could contain a different ingredient of growth medium. Alternately, a common growth medium can be used in all of the growth sections and a different concentration of sample would be applied to each longitudinal section.

Figure 11:
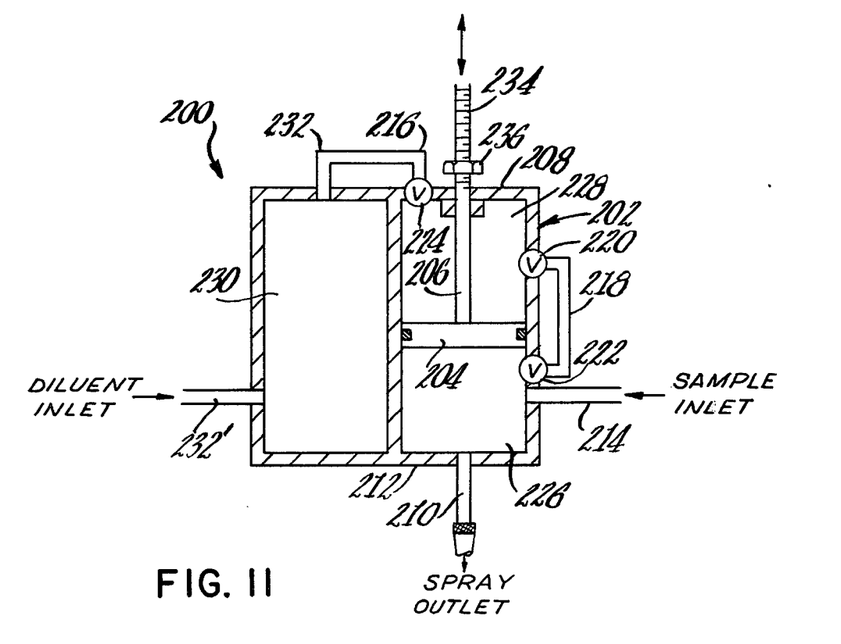
FIG. 11 is a schematic elevational view of a piston and cylinder arrangement utilized for serial dilution in accordance with the present invention.

Referring now to FIG. 11, there is shown another embodiment of a device for providing serial dilutions. The device shown generally at 200 includes a cylinder 202 with a piston 204 movable within the cylinder. A rod 206 is coupled to the piston and extends through the top wall 208 of the cylinder. The rod is utilized for reciprocally operating the piston in the cylinder.

An outlet 210, shown as a spray outlet is provided in the bottom 212 of the cylinder. A first inlet 214 is located intermediate the lower wall 212 and the piston 214 for receiving a microbiological sample. A second inlet 216 is provided on the upper wall 208 which can receive diluent. A one-way passage 218 is provided in the side wall of the cylinder permitting passage from the upper side of the piston to the lower side of the piston. The one way passage is controlled by means of valves 220 and 222 and the passageway 216 is controlled by the valve 224. In operation, the microbiological sample is fed through the inlet 214 and diluent is continuously provided available through the inlet 216. As the rod reciprocates, serial dilution will occur.

Specifically, as the rod is lowered, the piston moves downward and a portion of the sample contained in the lower chamber 226 is sprayed out through the outlet 210. As the piston moves upward, a portion of the diluent contained in the upper chamber 228 of the cylinder passes through the one-way passageway 218 into the lower chamber 226 to mix with the sample and dilute the sample. On the next downward stroke of the piston, a portion of the diluted sample will flow out of the spray outlet 210.

On the subsequent upward stroke of the piston, again a portion of the diluent contained in the upper chamber 228 will pass through the one-way passage 218 and now the previously diluted sample in the lower chamber will be further diluted by the additional diluent. Again, the downward stroke will force the now higher diluted sample out of the spray outlet.

In this manner, the continuous reciprocating motion of the piston provides serial dilutions of the sample.

In order to facilitate the continued supply of diluent, and provide a free standing unit, a second chamber 230 is interconnected to the cylinder by means of the passageway 232. Initially, the adjacent chamber 230 is filled with diluent. Alternately, an inlet 23' can be provided in the adjacent chamber and diluent inputted to the adjacent chamber. With each downward stroke of the piston, additional diluent is fed from the adjacent chamber 230 into the top chamber 228 of the cylinder to provide a continued supply of diluent for the serial dilutions.

The top end of the rod 206 can be threaded at 234 and a nut 236 placed appropriately along the threaded portion to control the downward stroke of the piston to thereby control the amount of diluted sample sprayed out of the device.

Each of the foregoing devices and apparatus, as well as the methods described, all form a part of a total microbiological system which can be integrated and utilized for the miniaturization and automation of a microbiological laboratory. At the same time, each device, apparatus, and/or method can be utilized individually to provide improved operation of at least that portion of the total system as is desired.

There has been disclosed heretofore the best embodiment of the invention presently contemplated. However, it is to be understood that various changes and modifications may be made thereto without departing from the spirit of the invention.

I claim:

1. A microbiological mixing and dilution device comprising, at least one fluid amplifier having a control chamber, a first inlet port for feeding a microbiological fluid sample from a source of supply into said control chamber, a second inlet port for feeding a fluid diluent from another source of supply into said control chamber wherein the fluid sample and the fluid diluent are mixed, two fluid outlet ports for selectively discharging the contents of said control chamber, said control chamber serving as a mixing chamber to dilute the sample and control port means fluidly coupled to said control chamber for utilizing a suitable control fluid to direct at least a portion of the diluted sample to a selected outlet port, and distribution means for receiving the diluted sample from said selected outlet port for microbiological use.

2. A microbiological device as in claim 1, further comprising means coupled to said control port means for initially directing all of the diluted sample to one outlet port and subsequently switching the sample to the other outlet port whereby a constant quantity of the diluted sample is discharged to a receiving well.

3. A microbiological dilution device comprising:

a fluid amplifier having a mixing chamber, an inlet port for feeding an aqueous microbiological liquid into said mixing chamber, two fluid outlet ports for selectively discharging the contents of said mixing chamber, and control port means fluidly coupled to said mixing chamber for utilizing a suitable control fluid to direct at least a portion of the aqueous microbiological liquid to said selected outlet port;

two input means fluidly coupled to said inlet port;

supply means for providing the aqueous microbiological liquid in the form of a microbiological sample to one input means and a diluent to the other input means for dilution of the sample in said mixing chamber, and output means for removing a predetermined volume of the diluted sample from one of said outlet ports and the remainder of the diluted sample from the other said outlet ports.

4. A microbiological dilution device as in claim 3 further comprising a plurality of fluid amplifiers each having two input means, said amplifiers being serially interconnected with a first one of said input means of each of said amplifiers being fluidly coupled to a first one of said outlet ports of a preceding amplifier, said supply means fluidly coupling the microbiological sample to a first one of said input means of only the first of said plurality of amplifiers and the diluent to the second one of said input means of each of said amplifiers, and said output means removing said predetermined volume of the diluted sample from said second one of said outlet ports of each of said amplifiers, whereby each fluid amplifier provides a further dilution of the sample which it receives from the preceeding amplifier to thereby achieve a serial dilution of the sample.

5. A microbiological dilution device as in claim 4, wherein said control port means individually controls the selected portion output of each of said amplifiers to thereby control the percent dilution of each portion.

6. A microbiological dilution device as in claim 3 further comprising baffle means in said mixing chamber to increase the mixing of the sample with the diluent.

7. A microbiological distribution device comprising: a plurality of serially connected fluid amplifiers each having a control chamber, an inlet port for feeding an aqueous microbiological liquid into said control chamber, first and second fluid outlet ports for selectively discharging the contents of said control chamber, and control port means fluidly coupled to said control chamber, for determining the flow of fluid into the respective outlet ports, one of said outlet ports of each of said amplifiers being fluidly coupled to said inlet port of said next successive amplifier, said other outlet port of each said amplifiers discharging into an array of receiving wells, said inlet port of the first of said amplifiers permitting fluid coupling to a source of an aqueous microbiological sample for distribution, selector control means simultaneously coupled to all of said control port means for initially directing all of the aqueous microbiological liquid to said first outlet port of each of said amplifiers and upon actuation said selector control means will simultaneously direct the aqueous microbiological liquid in each amplifier to said second outlet port, whereby the aqueous microbiological liquid will serially flow through all of said amplifiers and after all of said amplifiers are filled the selector control means is actuated and the aqueous microbiological liquid will switch to said second outlet port, whereby a substantially equal volume of aqueous microbiological liquid will be discharged from each of said amplifiers into the receiving wells.

8. A microbiological distribution devices as in claim 7 further comprising detecting means for detecting when all said amplifiers have been filled with the working liquid, said selector control means being responsive to said detecting means for switching the liquid to said other outlet ports.

9. A microbiological distribution device as in claim 7 further comprising a microbiological tray having a base portion and a cover portion, an array of receiving wells formed in said base portion, said plurality of serially connected fluid amplifiers being formed in said cover portion with said other outlet ports of each amplifier being positioned over one of the receiving wells.

10. A microbiological distribution device as in claim 9, wherein said cover portion comprises an inlet coupler for connection to said supply means, control couplers for connection to said selector control means, and a discharge coupler connected to said one outlet port of the final one of said plurality of amplifiers.

11. A serial dilution microbiological device comprising: a cylinder;

a piston reciprocally movable in said cylinder and separating said cylinder into first and second chambers one on each side of the piston, the reciprocating of the piston within the cylinder changing the volume of the chambers inversely with respect to each other, said piston preventing fluid flow therethrough between the chambers, a rod coupled to said piston for reciprocally operating said piston within said cylinder, an output from said first chamber in said cylinder, an inlet into said first chamber for receiving a microbiological sample into said first chamber, an inlet into said second chamber for receiving diluent into said second chamber, and a one-way pasage between said first and said second chambers permitting flow only from said second chamber into said first chamber, whereby reciprocation of said piston provides a serially diluted sample at the output of said cylinder.

12. A microbiological device as in claim 11 further comprising a diluent reservoir and another one-way passage fluidly coupled between said reservoir and said inlet of said second chamber for flow of diluent into said second chamber.

13. A microbiological device as in claim 11 further comprising limiting means coupled to said rod for determining the length of the stroke of said piston within said cylinder.

* * * * *